United States Patent
Laughlin et al.

[11] Patent Number: 5,732,485
[45] Date of Patent: Mar. 31, 1998

[54] FOOT AND SHOE DEODORIZER

[75] Inventors: Thomas J. Laughlin, Germantown; Gerald R. Dever, Cordova; William S. Rogers, Memphis, all of Tenn.

[73] Assignee: Schering-Plough Healthcare Products, Inc., Memphis, Tenn.

[21] Appl. No.: 535,271

[22] PCT Filed: Apr. 11, 1994

[86] PCT No.: PCT/US94/03692
§ 371 Date: Oct. 10, 1995
§ 102(e) Date: Oct. 10, 1995

[87] PCT Pub. No.: WO94/23766
PCT Pub. Date: Oct. 27, 1994

Related U.S. Application Data

[63] Continuation of Ser. No. 48,047, Apr. 13, 1993, abandoned.

[51] Int. Cl.$^6$ .................. A43B 23/00; A43B 13/38
[52] U.S. Cl. .................. 36/136; 36/3 B; 36/43
[58] Field of Search ............... 36/136, 3 B, 3 R, 36/3 A, 43, 132

[56] References Cited

U.S. PATENT DOCUMENTS

| | | | |
|---|---|---|---|
| 1,480,234 | 1/1924 | Wedd | 36/3 B |
| 2,200,849 | 5/1940 | Margolin | 36/3 R |
| 2,565,028 | 8/1951 | Keithley, Jr. | 36/3 A |
| 2,973,286 | 2/1961 | Ulrich . | |
| 3,655,129 | 4/1972 | Seiner . | |
| 3,685,734 | 8/1972 | Paciorek et al. . | |
| 4,051,159 | 9/1977 | Tsoucalas et al. . | |
| 4,161,284 | 7/1979 | Rattan . | |
| 4,283,011 | 8/1981 | Spector . | |
| 4,284,444 | 8/1981 | Bernstein et al. . | |
| 4,316,333 | 2/1982 | Rothschild . | |
| 4,419,396 | 12/1983 | Sugimoto . | |
| 4,493,869 | 1/1985 | Sweeny et al. . | |
| 4,605,592 | 8/1986 | Paquette et al. . | |
| 4,654,256 | 3/1987 | Doree et al. . | |

(List continued on next page.)

FOREIGN PATENT DOCUMENTS

| | | |
|---|---|---|
| 0 103 407 A1 | 3/1984 | European Pat. Off. . |
| 0213 737 A1 | 7/1986 | European Pat. Off. . |
| 0 272 690 A2 | 6/1988 | European Pat. Off. . |
| 0 300 084 A2 | 1/1989 | European Pat. Off. . |
| 1.455.904 A | 10/1966 | France . |
| 451 950 | 10/1927 | Germany . |
| 17 18 084 | 10/1955 | Germany . |
| 32 33 006 A1 | 3/1984 | Germany . |
| 35 16 653 A1 | 11/1986 | Germany . |
| 2 183 479 | 6/1987 | United Kingdom . |
| WO 79/01013 | 11/1979 | WIPO . |
| WO 89/07429 | 8/1989 | WIPO . |
| WO 90/04339 | 5/1990 | WIPO . |

OTHER PUBLICATIONS

Environmental Odor Control; Robert T. Maleeny and William F. Palmer; pp. 28–30 (1991).
Elucidation of chemical compounds responsible for foot malodour; British Journal of Dermatolgoy (1990) 122, 771–776; F. Kanda, et al.
GAF Corporation's Handbook of Water–Soluble Gums and Resins by Robert L. Davidson titled Polyvinylpyrrolidone Copy of Chapter 21 pp. –21–1 through 21–21, (1980).
AWEAR™ product specification Thermedics Inc. pp. 1 and 2, pre –1990.

*Primary Examiner*—Ted Kavanaugh
*Attorney, Agent, or Firm*—Joseph T. Majka

[57] ABSTRACT

A deodorizer for masking foot and shoe odors through controlled release of fragrance is claimed.

17 Claims, 2 Drawing Sheets

U.S. PATENT DOCUMENTS

| | | |
|---|---|---|
| 4,694,590 | 9/1987 | Greenawalt . |
| 4,696,844 | 9/1987 | Spector . |
| 4,710,536 | 12/1987 | Klingen et al. . |
| 4,714,655 | 12/1987 | Bordoloi et al. . |
| 4,720,409 | 1/1988 | Spector . |
| 4,735,010 | 4/1988 | Grinarml . |
| 4,737,410 | 4/1988 | Kantner . |
| 4,749,590 | 6/1988 | Klingen et al. . |
| 4,774,133 | 9/1988 | Doree et al. . |
| 4,813,157 | 3/1989 | Boisvert et al. . |
| 4,814,212 | 3/1989 | Spector . |
| 4,841,648 | 6/1989 | Shaffer et al. . |
| 4,874,129 | 10/1989 | DiSapio et al. . |
| 4,889,755 | 12/1989 | Charbonneau . |
| 4,898,633 | 2/1990 | Doree et al. . |
| 4,943,461 | 7/1990 | Karim . |
| 4,959,208 | 9/1990 | Chakrabarti et al. . |
| 5,154,682 | 10/1992 | Kellerman . |
| 5,184,410 | 2/1993 | Hamilton ........................ 36/138 X |
| 5,261,169 | 11/1993 | Williford ........................ 36/43 |

FOOT AND SHOE DEODORIZER

The present application is the United States national application corresponding to International Application No. PCT/US 94/03692, filed Apr. 11, 1994 and designating the United States, which PCT application is in turn a continuation of U.S. application Ser. No. 08/048,047, filed Apr. 13, 1993 now abandoned the benefit of which applications are claimed pursuant to the provisions of 35 U.S.C. 120,363 and 365 (C).

BACKGROUND

According to Robert T. Maleeny and William F. Palmer, Environmental Odor Control, Soap/Cosmetics/Chemical Specialties for January 1991, pp. 28–31, malodors are usually caused by chemicals that are perceived at very low concentrations. Although malodors may not be dangerous to health at low levels, they can affect one's enjoyment of the environment. Maleeny and Palmer disclose that the perfumers of ancient Egypt and Medieval Europe practised masking by deodorizing through the use of perfumes, colognes and sachets. The authors also suggested that foot care can be one of many applications for malodor counteractants. However, there are few, if any commercially available perfume deodorizers in which the perfume component of the deodorizer can be releasably attached to and removed from the interior of a shoe, and still provide sufficient perfume to mask foot or shoe odors. Part of the problem of constructing such a deodorizer lies in the relatively high loading of fragrance in the component containing the perfume (ie. about 10 milligrams (mg) or greater) necessary to mask the foot and shoe odors. Such concentrated loadings of fragrance in the perfume component can cause the adhesive holding the deodorizer to the footwear to soften, causing the deodorizer to loosen from the footwear. In view of the foregoing, it would be desirable to provide a convenient deodorizer for masking foot and shoe odors in which the perfume component could be easily applied to and removed from the shoe interior. It would also be desirable to provide a deodorizer for masking foot and shoe odors through controlled release of fragrance.

SUMMARY OF THE INVENTION

In one embodiment, the present invention is directed toward a deodorizer for masking foot and shoe odors, comprising:

a) a retainer having an opening defined by an edge;
b) means for securing the retainer to the interior surface of a shoe;
c) a patch containing fragrance in amounts effective to mask foot and shoe odors, wherein the patch is held in place within the retainer opening by contact of the edge of the fragrance patch with the edge of the retainer opening.

Preferably, the retainer and patch are circular in shape. Also preferred is that the means for securing said retainer to the interior of a shoe is a pressure-sensitive adhesive. In a more preferred embodiment, the patch is made from a carrier containing a mixture of fragrance and polymer binder. Preferably both the carrier and the retainer are made of a non-woven felt, such as derived from polypropylene fibers. Also preferred is that the amount of fragrance in the patch ranges from about 10 milligrams or greater. Also preferred is that the polymer binder is polyvinylpyrrolidone.

In another embodiment, the present invention is directed towards an insole/deodorizer for cushioning a foot and deodorizing foot and shoe odors comprising:

a) a cushioning insert having opening defined by an edge; and
b) a patch containing fragrance in amounts effective to mask foot and shoe odors, wherein the patch is held in place within the insert opening by contact of the edge of the fragrance patch with the edge of the insert opening.

In yet another embodiment, the present invention is directed toward a method for deodorizing foot and shoe odors comprising attaching to the interior of a shoe a deodorizer, wherein the deodorizer comprises:

a) a retainer having an opening defined by an edge;
b) means for securing the retainer to the interior surface of a shoe;
c) a patch containing fragrance in amounts effective to mask foot and shoe odors, wherein the patch is held in place within the retainer opening by contact of the edge of the fragrance patch with the edge of the retainer opening.

In yet another embodiment, the present invention is directed toward a method for cushioning a foot and deodorizing foot and shoe odors comprising inserting into a shoe an insole/deodorizer wherein the insole/deodorizer comprises:

a) a cushioning insert having opening defined by an edge; and
b) a patch containing fragrance in amounts effective to mask foot and shoe odors, wherein the patch is held in place within the insert opening by contact of the edge of the fragrance patch with the edge of the insert opening.

The present invention has the advantage of masking undesirable odors in a shoe by the controlled release of fragrance lasting over a normal day's wear. A second advantage is that the controlled fragrance release can be triggered by moisture from the foot, thus minimizing fragrance loss from the patch prior to application to the foot or footwear. Where a felt carrier is employed, a third advantage of present invention is that it reduces the tackiness at the exposed surface of the fragrance patch. A fourth advantage of the present invention is that the patch containing the fragrance is easy to insert and remove with the need for little or no adhesive since the patch utilizes its edge or periphery to hold it in place. A fifth advantage of the present deodorizer is that it will stay secured to the footwear even when the deodorizer is moistened or made wet.

DETAILED DESCRIPTION OF THE INVENTION

Figure 1:
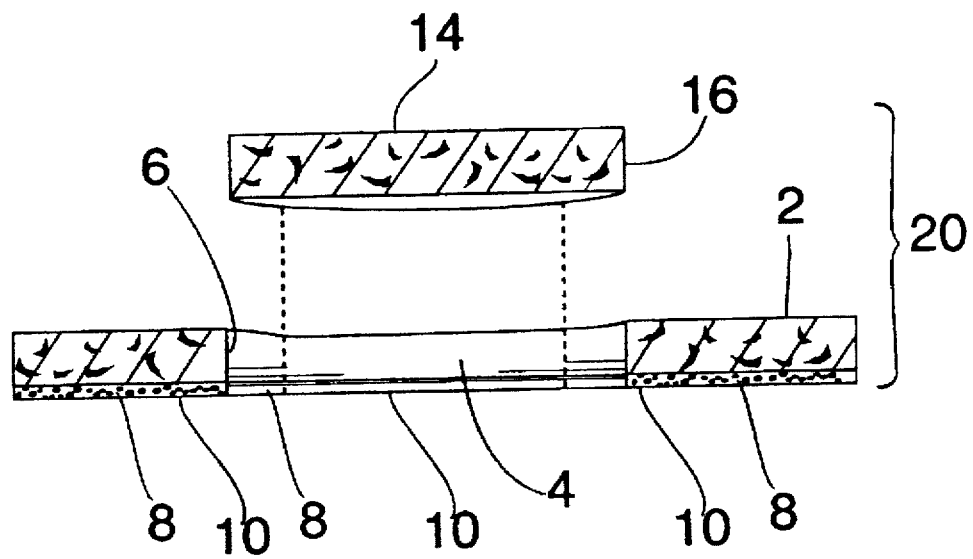
FIG. 1 illustrates an exploded view of deodorizer 20. Deodorizer 20 is made of retainer 2 having an opening 4 defined by an interior edge 6. To the underside of retainer 2 is bonded the means for securing retainer 2 to the shoe, eg. pressure sensitive adhesive 8. The adhesive secures retainer 2 to the interior surface of a shoe or other footwear. To retainer 2 is fitted a patch 14 containing fragrance in amounts effective to mask foot and shoe odors. In this embodiment, edge 16 of patch 14 approximates the size and shape of retainer opening 4. Fragrance-containing patch 14 is held in place within retainer opening 4 by contact of edge or periphery 16 of fragrance patch 14 with edge 6 of retainer opening 4. During packaging and storage of deodorizer 20, adhesive 8 is typically covered with a release liner, not shown. When the fragrance in patch 14 is used up or is no longer effective, patch 14 can be easily removed from retainer 2, for example, by prying with a fingernail or by gently pinching and lifting the exposed surface of patch 14. The used patch can be replaced with a fresh fragrance patch 14. Thus, patch 14 is releasably attached to retainer 2.
Figure 2:
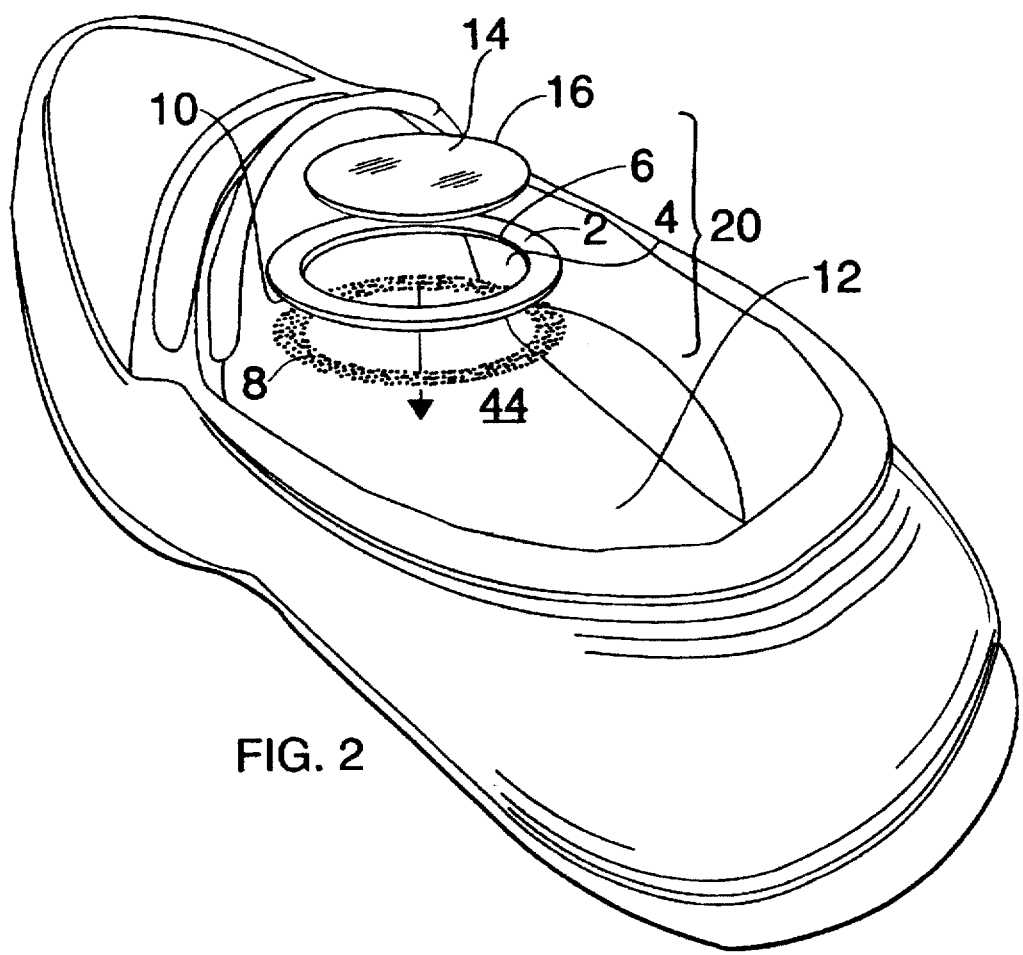
FIG. 2 illustrates an interior view of a man's casual shoe in which deodorizer 20 is secured to shoe insole 12 at arch area 44. Retainer 2 is bonded to arch area 44 via adhesive 8 on the underside 10 of retainer ring 2. Retainer 2 has opening 4 defined by edge 6. Fragrance containing patch 14 is inserted into retainer opening 4 and held in place within opening 4 by contact of edge 6 of deodorizer patch 14 with edge 6 of retainer 2.
Figure 3:
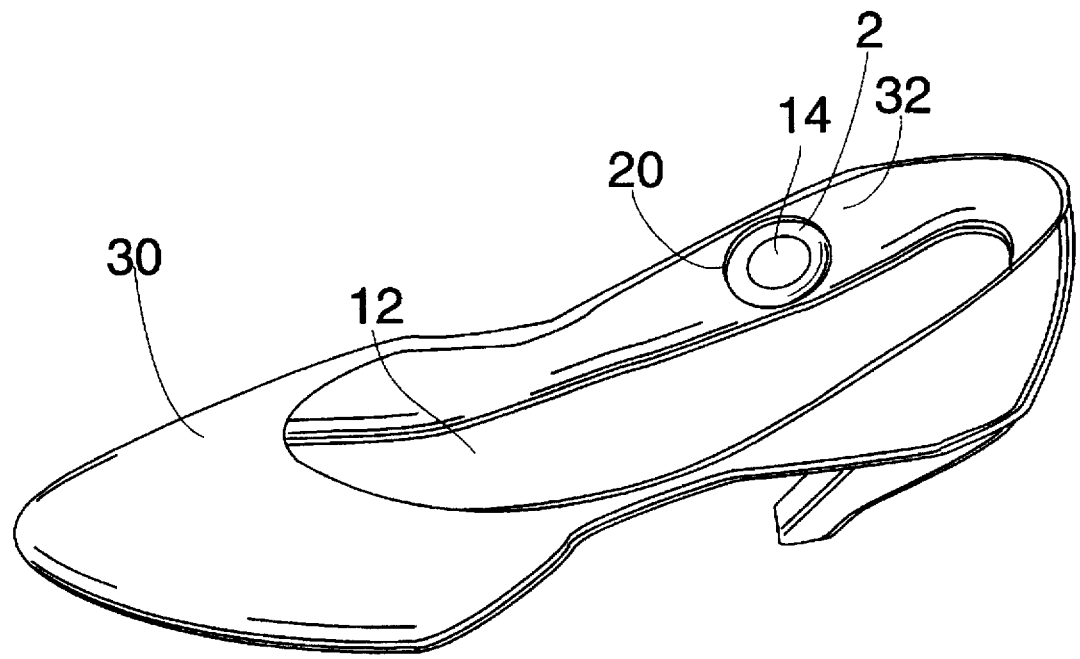
FIG. 3 illustrates a view of a woman's dress shoe 30 in which a fully assembled deodorizer 20 is secured to an interior side wall 32 of the shoe upper. Fragrance patch 14 is held in place within the retainer opening by contact of the edge of the fragrance patch 14 with the edge of retainer 2.
Figure 4:
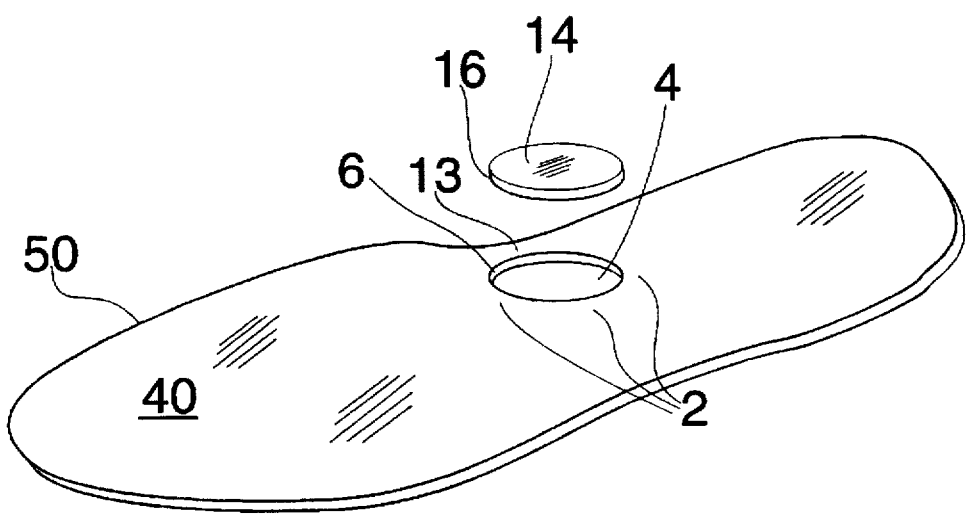
FIG. 4 shows insole/deodorizer 50. In this embodiment, insert 40 which serves as the retainer for holding fragrance patch 14. Retaining insert 40 has opening 4 located in arch area 13 into which fragrance patch 14 is inserted and held in place by contact of edge 16 of fragrance patch 14 with edge 6 of insert opening 4. In another embodiment, the bottom of opening 4 could be contoured to have a ledge (not shown) upon which fragrance patch 14 could rest upon.

For purposes of this invention, the term "shoe" includes any article for the foot to which the deodorizer can be attached, or the insole/deodorizer inserted, such as men's and women's shoes, sneakers, insoles, arch supports, athletic footwear, sandals and the like.

The deodorizer, retainer and/or patch can be formed into any convenient geometric shape or aesthetic design, such as circles, ovals, squares, triangles, stars, flowers, animal-shapes, baseballs, basketballs, soccer balls, footballs, hockey pucks, faces, characters and the like. The patch can be of a circular shape or disk-shaped, about 2 to 3 centimeters (cm) in diameter. The deodorizer, retainer and/or patch can be made to any suitable thickness, such from about 1 to about 5 millimeters, more preferably about 2 to 3 millimeters thickness. Similarly, the deodorizer, retainer and/or patch can be covered with any materials which provide a suitable design or illustration, to enhance the appearance of the deodorizer. Generally, but not necessarily, the edge or periphery of the patch can approximate the size and/or shape of the retainer or insert opening. For example, a round patch could be fitted into a round retainer opening, although a round patch could also be fitted to a square retainer opening.

The retainer is the structural component of the deodorizer which retains or holds the fragrance-containing patch in held in place. The retainer can be made from any suitable material, including foams, non-woven felts and fabrics, woven fabrics, molded rubbers, leather, and cellulosic substrates. Suitable foams include polyethylene foams, latex foams, vinyl foams and polyurethane foams. Suitable non-woven felts include natural felts such as wool and cotton and synthetic felts such as polypropylene, acrylic, polyester and nylon. Suitable fabrics include corduroy and moleskin. The retainer can be secured to the shoe interior by any suitable means, such as by stitching, staples or adhesives, preferably a pressure sensitive adhesive. Alternatively, where the insert retains the fragrance patch, the insert can be made from any materials suitable for making insoles.

The carrier is the structural component of the fragrance-containing patch which supports or carries the fragrance and/or polymer. The carrier can be made of fibrous materials including polypropylene felt, woven and non-woven materials, fabrics, microporous membranes (diffusion loaded), fused microcapsules (encapsulated), monolith films (cast blends of polymer and fragrance) or films of polymers which form molecular associations with the fragrance. Suitable microporous membranes include microporous polyethylene films into which fragrances are diffusion loaded. Preferably, the carrier is a non-woven felt of polypropylene fibers forming a thickness of about 20 to about 100 mils thickness, preferably about 50–75 mils thickness. A felt carrier has the advantage of being able to reduce the oily feel imparted by the fragrance as well as providing enhanced surface area for coating with fragrance/polymer matrices. Also preferred is that the carrier is coated with selected polymer/fragrance blends.

Fragrances employed in the present patch can include any commercial or proprietary fragrance, preferably a "baby-powder" fragrance, a citrus fragrance or a green herbal fragrance. The amount of fragrance used in each patch should be sufficient to mask foot and shoe odors for about one day to one week. The amount of fragrance can range from about 10 mg to about 80 mg fragrance, preferably about 20 to about 70 mg fragrance, most preferably about 30 to 50 mg of fragrance per patch.

The fragrance can be entrapped into any suitable polymer which can be coated on the carrier. Alternatively, the fragrance can be incorporated into the carrier itself. Where a polymer is employed, suitable polymers include those prepared from poly(vinyl pyrrolidone), acrylics or hydrogels. Polyvinylpyrrolidone (PVP) is a polymer that possesses unusual complexing and colloidal properties and is physiologically inert, as described in The Handbook of Water-Soluble Gums and Resins by Robert L. Davidson, Chapter 21—"Polyvinylpyrrolidone", McGraw-Hill, Inc. (1980), pp 21-1 to 21-21, whose preparative teachings are incorporated herein by reference. Hydrogels can be derived from the interaction of polyvinylpyrrolidone with urethanes, giving a water swellable material which is slippery when wet. The polyvinylpyrrolidone in the hydrogel is capable of forming complexes with polar materials by hydrogen bonding and can form stable complexes with hydrophobic materials by van der Waals interactions. A commercially available hydrogel is known as Hydromers®, trademark of Hydromer Inc., Salem Industrial Park, Whitehouse, N.J. Such hydrogels can form excellent films on the carrier even when blended with fragrance.

Preferably, a mixture of the fragrance and a suitable polymer such as polyvinylpyrrolidone are added to the carrier. The fragrance/polymer mixture increases the viscosity of the fragrance, thus facilitating the application of the fragrance to the carrier. The fragrance/polymer mixture has the additional advantage of retarding the evaporation or release of fragrance from the fragrance patch during storage, thus ensuring that the requisite amount of fragrance will be available for deodoring foot and shoe odors, particularly after the packaging containing the fragrance patch is opened. The mixture also enables the fragrance to associate with the carrier to give a triggered release, ie. time, heat, moisture and pressure, depending upon the type of carrier employed. For example, the use of polyvinylpyrrolidone can give a moisture-triggered release, where the fragrance associated with the polymer can be dispaced by water, thus releasing the fragrance. Other polymers or microencapsulation systems can give a temperature- or pressure-triggered release.

Typically, the fragrance is incorporated into the carrier by blending or mixing the fragrance with a polymer and adding the fragrance/polymer mixture to the carrier. Any suitable solvent can be employed for mixing the fragrance with the polymer, including alcohols of such as methanol, ethanol and isopropanol, most preferably methanol. The solvent can be employed in amounts sufficient to solubilize the polymer and can range from about 30 to about 70 percent or more solvent, more preferably about 50 percent solvent.

To construct a moisture-triggered patch, the fragrance is blended into a suitable hydrophilic polymer. The fragrance binds to the hydrophilic polymer, but not as strongly as water would. When the complex is exposed to water, the fragrance is displaced and is free to evaporate to mask unpleasant foot or shoe odors.

Where a pressure sensitive adhesive is employed, the adhesive preferably is strong enough to hold the retainer to the shoe interior for about one week to 1–3 months or more. Adhesives which could be used for the shoe deodorizer patch include but are not limited to the following:

A. Solvent-based acrylic adhesives such as:

Monsanto GMS 737, trademark of Monsanto Corporation, St. Louis, Mo.;

National Starch Durotak 72-9720 and 80-1197, trademark of National Starch & Chemical Corp., Bridgewater, N.J.

Ashland's AROSET 1113-AD-40 and 1085-Z-45, trademark of Ashland Oil Co., Ashland, Ky.

B. Solvent-based rubber adhesives such as:

National Starch 36-6172

C. Acrylic emulsion adhesives such as:

Monsanto GME 2397

Rohm & Haas N580, trademark of Rohm & Haas Co., Philadelphia, Pa.

Unocal 76 RES 9646, trademark of Unocal Corp., Los Angeles, Calif.;

Ashland's AROSET 2022-W-50

D. Adhesive Transfer Tapes such as:

3M F-9465 PC, trademark of 3M Co., St. Paul, Minn.

Avery-Denison MED 1116, trademark of Avery Dennison Corp., Pasedena, Calif.

ARCare 7530, trademark of Adhesive Research Inc., Glen Rock, Pa.; and

RX230U, trademark of Coating Science Inc., Bloomfield, Conn.

A tackifier is a substance which enhances the property of tack of a pressure sensitive adhesive. Suitable tackifiers include rosin acid derivatives, terpene based derivatives and synthetic C-5 tackifiers such as Escorez 1310 of the Exxon Corporation, Irving, Tex. The amount of tackifier in the adhesive can range from about 10 to about 60% by weight of the adhesive, preferably from about 20 to about 40%.

Polybutene is a known short chain oligomer which serves to plasticize the high molecular weight polyisobutene. The amount of polybutene in the adhesive can range from about 10 to about 40% by weight, preferably from about 20 to about 30%. For example a suitable polybutene is H-1500 of the Amoco Corporation, Chicago, Ill.

Polyisobutylene is a high molecular weight polymer or resin which serves as the primary structural component of the adhesive. The amount of polyisobutene in the adhesive can range from about 30 to about 80% by weight of the composition. Other ranges within the above range can vary, depending upon the amounts of tackifier and polybutene used.

A release liner should be used to prevent contamination of the adhesive prior to its contact with the footwear. Suitable release liners include high density polyethylene (HDPE), polyester (ie. Mylar®), polyethylene terephthalate (PET) and the like, preferably 7 mil high density polyethylene film.

The following examples are intended to illustrate, but not limit the invention.

EXAMPLE 1

Preparation of a Moisture Triggered, Foot Deodorizer Patch

| | |
|---|---|
| Fragrance patch | 1.9 cm (¾ inch) diameter felt patch (polypropylene felt, 330 g/m² (10 oz/ square yard), 1.9 mm (75 mil) thickness) 40 mg of fragrance (Green Herbal coated with a 1:2 blend of fragrance:PVP. |
| Retainer | felt ring (polypropylene felt) with 1.9 cm (¾ inch) inner diameter and 2.9 cm (1 ⅛ inch) outer diameter laminated with 0.0254 mm (1 mil) of a solvent based acrylic pressure-sensitive adhesive. |

A retainer ring is adhered on the inside panel above the arch area of the upper of a shoe. The fragrance-containing patch is inserted into the retainer ring. The shoe is worn under normal use. After the fragrance patch is no longer effective, typically after about one week, the used fragrance patch is removed and replaced with a fresh fragrance containing patch. During the entire six-weeks of testing where the fragrance-containing patch is replaced weekly, the foot and shoe are effectively deodorized. Upon completion of testing, the retainer ring is removed from the shoe upper with no adhesive residue left on the shoe.

EXAMPLE 2

Essentially the same foot and shoe deodorizer as in Example 1 is prepared, except that the retainer ring is made from 1.65 mm (65 mil) thickness low-density polyethylene foam.

EXAMPLE 3

| | |
|---|---|
| Fragrance patch: | 2.2 cm (⅞ inch) diameter felt patch (polypropylene felt, 263 g/m² (8 oz/square yard), 1.27 mm (50 mils) thickness) 50 mg of fragrance (green herbal) coated with a 1:1 blend of fragrance:PVP |
| Retainer: | felt ring (same as above) with 2.2 cm (⅞ inch) inner diameter and a 3.2 cm (1 ¼ inch) outer diameter laminated to 0.0254 mm (1 mil) solvent based rubber pressure-sensitive adhesive. |

Essentially equivalent deodorizing performance as in Example 1 is attained.

We claim:

1. A deodorizer for masking foot and shoe odors, comprising:

a) a retainer having an opening defined by an edge;

b) a pressure sensitive adhesive for securing said retainer to the interior surface of a shoe;

c) a patch comprising a carrier, fragrance and polymer, wherein said fragrance is admixed with said polymer to retard evaporation or release of fragrance from the patch during storage and said carrier carries said fragrance and polymer, wherein the patch is held in place within the retainer opening by contact of the edge of the fragrance patch with the edge of the retainer opening and a surface of the patch is exposed so that patch can be easily removed from the retainer by prying the patch from the retainer with a fingernail or by gently pinching and lifting the exposed surface of the patch.

2. The deodorizer of claim 1 wherein the retainer and patch are circular in shape.

3. The deodorizer of claim 1 where the retainer is made of a non-woven felt.

4. The deodorizer of claim 3 wherein the non-woven felt is derived from polypropylene.

5. The deodorizer of claim 1 wherein the carrier is a non-woven felt.

6. The deodorizer of claim 1 wherein the carrier is polypropylene felt.

7. The deodorizer of claim 1 wherein the amount of fragrance in the patch ranges from about 10 milligrams to about 80 milligrams.

8. The deodorizer of claim 1 wherein the amount of fragrance in the patch ranges from about 30 to about 50 milligrams.

9. The deodorizer of claim 1 wherein the polymer is polyvinylpyrrolidone.

10. An insole/deodorizer for cushioning a foot and deodorizing foot and shoe odors comprising a) an insole having opening defined by an edge; and b) a patch comprising a carrier, fragrance and polymer wherein said fragrance is admixed with said polymer to retard evaporation or release of fragrance from the patch during storage and said carrier carries said fragrance and polymer, wherein said fragrance is in an amount effective to mask foot and shoe odors, wherein the patch is held in place within the insert opening by contact of the edge of the fragrance patch with the edge of the insert opening and a surface of the patch is exposed so that patch can be easily removed from the retainer by prying the patch from the retainer with a fingernail or by gently pinching and lifting the exposed surface of the patch.

11. The insole/deodorizer of claim 10 wherein the carrier is a non-woven felt.

12. The insole/deodorizer of claim 10 wherein the carrier is polypropylene felt.

13. The insole/deodorizer of claim 10 wherein the amount of fragrance in the patch ranges from about 10 milligrams to about 80 milligrams.

14. The insole/deodorizer of claim 10 wherein the amount of fragrance in the patch ranges from about 30 to about 50 milligrams.

15. The insole/deodorizer of claim 10 wherein the polymer is polyvinylpyrrolidone.

16. A method for deodorizing foot and shoe odors comprising attaching to the interior of a shoe a deodorizer, wherein the deodorizer comprises:

a) a retainer having an opening defined by an edge;

b) means for securing said retainer to the interior surface of a shoe;

c) a patch comprising a carrier, fragrance and polymer wherein said fragrance is admixed with said polymer to retard evaporation or release of fragrance from the patch during storage and said carrier carries said fragrance and polymer, wherein said fragrance is in an amount effective to mask foot and shoe odors, wherein the patch is held in place within the retainer opening by contact of the edge of the fragrance patch with the edge of the retainer opening and a surface of the patch is exposed so that patch can be easily removed from the retainer by prying the patch from the retainer with a fingernail or by gently pinching and lifting the exposed surface of the patch.

17. A method for cushioning a foot and deodorizing foot and shoe odors comprising inserting into a shoe an insole/deodorizer wherein the insole/deodorizer comprises:

a) a cushioning insole having opening defined by an edge; and b) a patch comprising a carrier, fragrance and polymer wherein said fragrance is admixed with said polymer to retard evaporation or release of fragrance from the patch during storage and said carrier carries said fragrance and polymer, wherein said fragrance is in an amount effective to mask foot and shoe odors, wherein the patch is held in place within the insert opening by contact of the edge of the fragrance patch with the edge of the insert opening and a surface of the patch is exposed so that patch can be easily removed from the retainer by prying the patch from the retainer with a fingernail or by gently pinching and lifting the exposed surface of the patch.

* * * * *